US006749887B1

United States Patent
Dick et al.

(10) Patent No.: US 6,749,887 B1
(45) Date of Patent: Jun. 15, 2004

(54) SOLUTION DRYING SYSTEM

(75) Inventors: Kenneth W. Dick, San Ramon, CA (US); Gary Otake, Union City, CA (US); Aaron Jessen, Campbell, CA (US)

(73) Assignee: LifeScan, Inc., Milpitas, CA (US)

( * ) Notice: Subject to any disclaimer, the term of this patent is extended or adjusted under 35 U.S.C. 154(b) by 166 days.

(21) Appl. No.: 09/996,631

(22) Filed: Nov. 28, 2001

(51) Int. Cl.[7] .................................................. B05D 3/00
(52) U.S. Cl. ...................................................... 427/2.13
(58) Field of Search ........................ 204/403.01–403.14, 204/416–419, 431; 205/775, 777.5, 778, 779, 787, 789, 789.5, 792; 422/50, 52, 57, 56, 82.01–82.03, 82.05, 82.06; 435/4, 40.5, 174–182; 427/2.11, 2.13

(56) References Cited

U.S. PATENT DOCUMENTS

| 4,224,125 A | | 9/1980 | Nakamura et al. | |
|---|---|---|---|---|
| 4,545,382 A | | 10/1985 | Higgins et al. | |
| 4,894,339 A | * | 1/1990 | Hanazato et al. | 435/182 |
| 4,935,346 A | | 6/1990 | Phillips et al. | |
| 4,938,860 A | * | 7/1990 | Wogoman | 204/403.05 |
| 5,221,457 A | * | 6/1993 | North et al. | 204/416 |
| 5,238,548 A | * | 8/1993 | van der Wal et al. | 204/418 |
| 5,266,179 A | * | 11/1993 | Nankai et al. | 204/401 |
| 5,284,570 A | * | 2/1994 | Savage et al. | 600/345 |
| 5,304,468 A | | 4/1994 | Phillips et al. | |
| 5,401,377 A | * | 3/1995 | Shieh et al. | 204/403.06 |
| 5,421,981 A | * | 6/1995 | Leader et al. | 204/403.13 |
| 5,563,031 A | | 10/1996 | Yu | |
| 6,193,873 B1 | | 2/2001 | Ohara et al. | |

FOREIGN PATENT DOCUMENTS

| WO | WO 97/18465 | 11/1996 |
|---|---|---|
| WO | WO 99/49307 | 3/1999 |

OTHER PUBLICATIONS

Y. Ci, F. Wang; Analytica Chimica Acta, 233 (1990), 299–302.

Kiyoshi Zaitsu, Yosuke Ohkura, "New fluorogenic substrates for Horseradish Peroxidase: rapid and sensitive assay for hydrogen peroxide and the Peroxidase" Analytical Biochemistry (1980) 109, 109–113.

* cited by examiner

*Primary Examiner*—Alex Noguerola
(74) *Attorney, Agent, or Firm*—Carol M. LaSalle; Bozicevic, Field & Francis, LLP

(57) ABSTRACT

A system for drying chemical reagents on material, particularly for producing product used in making reagent test strips is described. By drying selected chemicals on substrate drawn past a radiant energy source (preferably an IR source), rapid drying may be achieved while obtaining high-quality product. Airflow sufficient to break or disturb a vapor boundary layer above drying solution may be provided to increase drying speeds. Any airflow provided should not disturb the surface of the solution. Still, air-impingement drying techniques may be employed in the system to finish drying reagent material once it is sufficiently dry to be stable in shape. The substrate upon which chemicals are dried may include a reflective coating to facilitate its use with high levels of radiant energy. A metallic or metalized substrate is advantageously used in producing electrochemical test strips. Such test strips may be used in conjunction with various kits and be conveniently read using known hand-held meters.

6 Claims, 4 Drawing Sheets

SOLUTION DRYING SYSTEM

FIELD OF THE INVENTION

This invention relates to approaches for drying chemical compositions deposited on substrate in solution form. The invention is particularly suited for drying solution to produce reagent test strips for use in analyte determination assays, especially for electrochemical determination of blood analytes.

BACKGROUND OF THE INVENTION

Analyte detection assays find use in a variety of applications including clinical laboratory testing, home testing, etc., where the results of such testing play a prominent role in the diagnosis and management of a variety of conditions. The more common analytes include glucose, alcohol, formaldehyde, L-glutamic acid, glycerol, galactose, glycated proteins, creatinine, ketone body, ascorbic acid, lactic acid, leucine, malic acid, pyruvic acid, uric acid and steroids, etc. Analyte detection is often performed in connection with physiological fluids such as tears, saliva, whole blood and blood-derived products. In response to the growing importance of analyte detection, a variety of analyte detection protocols and devices for both clinical and home use have been developed. Many detection protocols employ a reagent test strip to detect analyte in a sample.

As the demand for reagent test strips has grown, the need for evermore efficient and flexible manufacturing approaches has increased. Still, little improvement has been made with respect to the handling of reagent material incorporated into test strips.

In producing reagent test strips, a coating of biological reagent which usually includes heat labile or moisture sensitive biological components (after drying for shelf stability) in a low viscosity aqueous solution is typically applied to a substrate used to produce one or more strips. Many existing systems designed to dry such biological reagents use high-velocity air impingement techniques to dry coating applied in aqueous form to a substrate. While effective to a certain extent, there are disadvantages associated with these currently employed techniques, typically due to low heat that may be applied and high air impingement rates necessary for drying in a reasonable amount of time.

As such, there is great interest in the development of new techniques for drying a liquid reagent composition with low viscosity and surface tension that has been applied to a substrate. The present invention satisfies this need by providing an improved approach to drying a liquid coating or composition applied to a substrate. Specifically, the present invention avoids problems commonly associated with high-velocity air impingement drying such as poor efficiency, slow desiccation, solution disturbance due to airflow. Various features of the invention offer increased manufacturing efficiency, a concomitant reduction in manufacturing cost and/or improved test strip quality. Further possible advantages of the present invention may also be apparent to those with skill in the art.

SUMMARY OF THE INVENTION

The present invention includes devices and methods for drying solution, typically having a viscosity less than 100 centipoises (cP), most often around 1.5 cP, that is applied to the surface of a material or substrate, especially for use in producing reagent test strips. Finished product made using the systems disclosed also form part of the invention. Typically, the product will be in the form of complete reagent test strips. Alternately, test strip precursors including at least substrate material with chemical solution dried thereon may be regarded as the product of the present invention.

The invention employs radiant energy to dry solution applied to a substrate. A non-disturbing airflow may be provided to enhance drying speed. Substrate with a chemical coating dried thereon according to the present invention may be used in a variety of types of test strips. Preferably, substrate processed according to the present invention preferably includes a metallic surface. Such a coating dramatically increases the potential for energy application. Furthermore, a metallic or metal-coated substrate is easily incorporated in electrochemical-type test strips.

BRIEF DESCRIPTION OF THE DRAWINGS

Each of the following figures diagrammatically illustrate aspects of the present invention. Variation of the invention from that shown in the figures is contemplated.

DETAILED DESCRIPTION OF THE INVENTION

Figure 1:
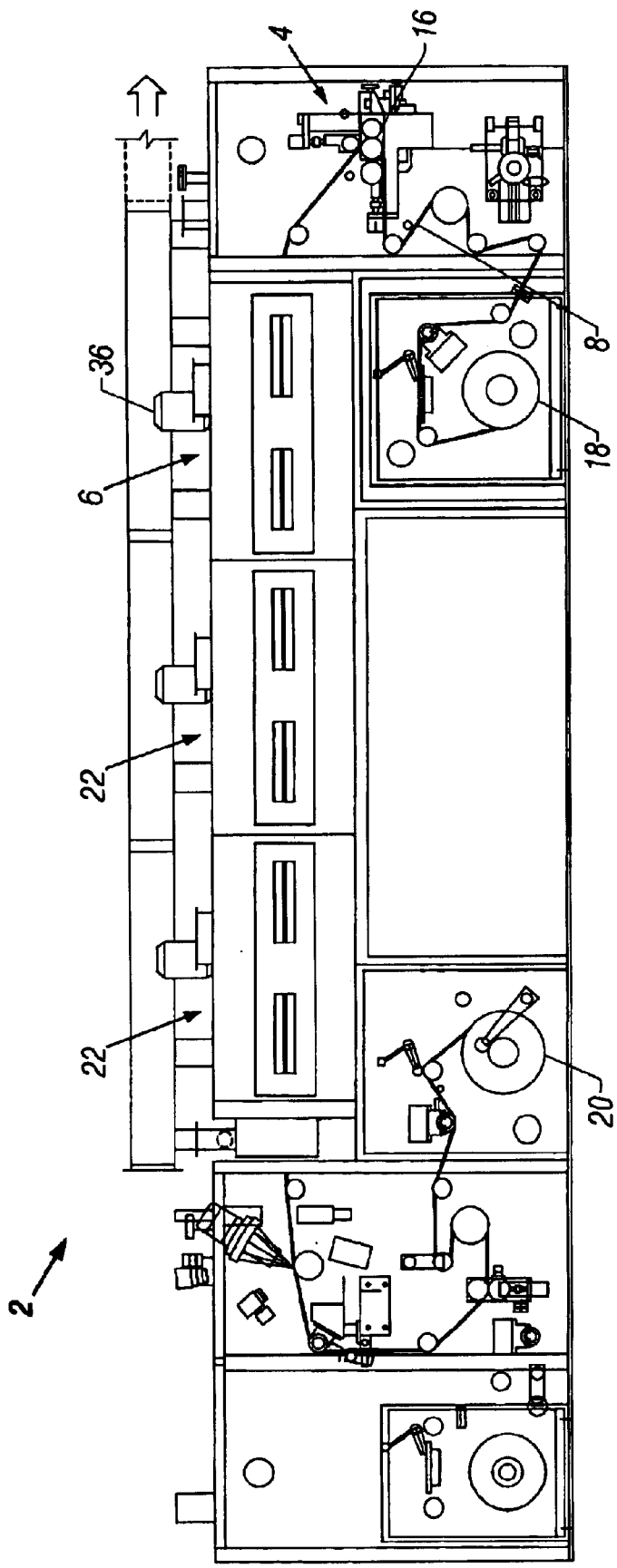
FIG. 1 shows an overview of the inventive system from the front side.

In describing the invention in greater detail than provided in the Summary above, the subject drying system and methods for its use are described first in greater detail, followed by a review of reagent test strip precursors that can be fabricated with using the subject system and methods, as well as the test strips produced from the subject test strip precursors and methods for using these test strips in analyte detection applications.

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims made herein. Furthermore, where a range of values is provided, it is understood that every intervening value, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention. Also, it is contemplated that any optional feature of the inventive variations described herein may be set forth and claimed independently, or in combination with any one or more of the features described herein.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All existing subject matter mentioned herein (e.g., publications, patents, patent applications and hardware) is incorporated by reference herein in its entirety. The referenced items are provided solely for their disclosure prior to the filing date of the present application. Nothing herein is to be construed as an admission that the present invention is not entitled to antedate such material by virtue of prior invention.

It is noted that as used herein and in the appended claims, the singular forms "a", "and", "said" and "the" include plural referents unless the context clearly dictates otherwise. Conversely, it is contemplated that the claims may be so-drafted to exclude any optional element. This statement is intended to serve as antecedent basis for use of such exclusive terminology as "solely," "only" and the like in connection with the recitation of claim elements or by use of a "negative" limitation Turning now to FIG. 1, elements of the present invention are shown in manufacturing system (2). The system shown is a model TM-MC3 system produced by Hirano Tecseed Co. Ltd (Nara, Japan) adapted for use in the present invention. Preferably, it includes such solution coating features in a coating section (4) as described in U.S. Patent Application, titled "Solution Striping System," to the inventors of the present system, filed on even date herewith.

Figure 2:
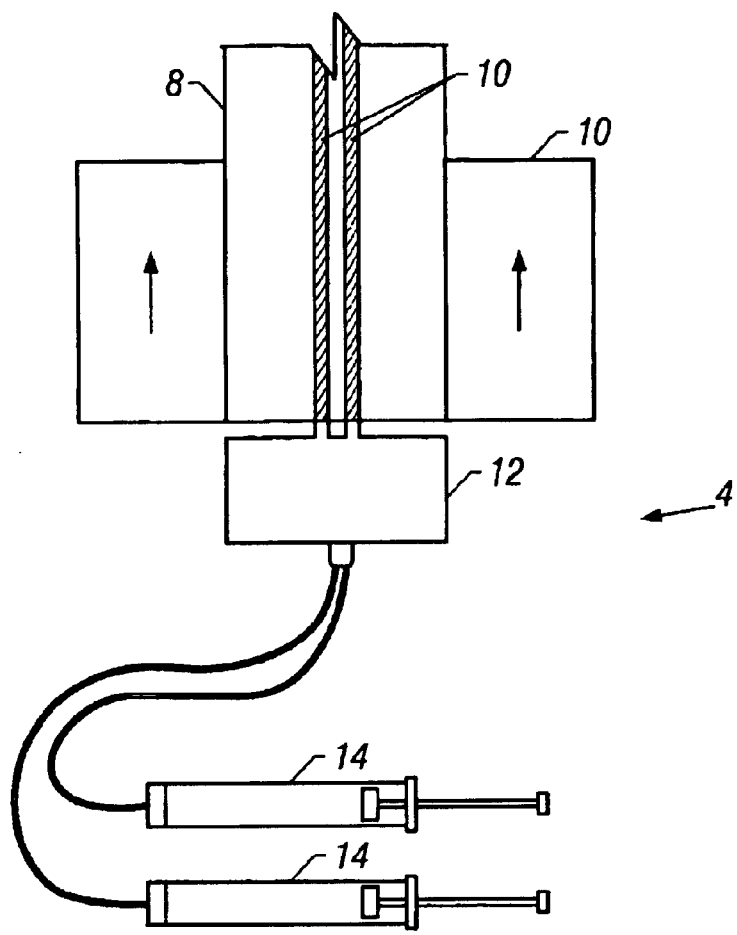
FIG. 2 shows a top view of material being coated by a coater section with solution for drying in an IR dryer section of the invention.

FIG. 2 shows a top view of features of the coating system preferably used in connection with the radiant energy drying system or section (6). In FIG. 2, a substrate or webbing material (8) is being coated which solution (10) fed to a die (12) by one or more pumps (14) to be deposited in the form of stripes or bands. A backing roller (16) is used to locate the webbing as it advances past the die in the direction indicated by the bold arrows.

As shown in FIG. 1, substrate (8) is provided in the form of a web by way of supply reel (18) and substrate with a reagent coating thereon is accumulated on a take-up real (20) after passing various guide rollers and passing through dryer section (6). One or more auxiliary dryer sections (22) may be provided in-line with dryer section (6) as well. These may include features like those in dryer section (6) or employ air-impingement drying techniques.

Preferably, the various dryer sections are provided behind a cover or within a housing as shown. Door(s) may be included for access. When employed in a radiant drier section, the structure will provide a shield from unnecessary exposure to radiant energy and act like the walls of an oven, re-radiating absorbed energy and speeding drying within. When employed in auxiliary dryer sections utilizing forced air for drying (especially, heated forced air), the structure provides a containment environment.

Substrate or webbing (8) preferably comprises a semi-rigid material that is capable of providing structural support to a test strip in which it may be incorporated. The substrate may comprise an inert material like a plastic (e.g., PET, PETG, polyimide, polycarbonate, polystyrene or silicon), ceramic, glass, paper, or plastic-paper laminate.

For use in an electrochemical test strip, at least the surface of the substrate that faces a reaction area in the strip will comprise a metal, where metals of interest include palladium, gold, platinum, silver, iridium, carbon, doped indium tin oxide, stainless steel and various alloys of these metals. In many embodiments, a noble metal such as gold, platinum or palladium is used.

In some instances, the substrate itself may be made of metal, especially one of those noted above. It is generally preferred, however, that the substrate comprise a composite of a support coated with a metallic and/or conductive coating (such as palladium, gold, platinum, silver, iridium, carbon conductive carbon ink doped tin oxide or stainless steel). For further discussion of substrate or support materials that find use in certain embodiments of the subject invention, see U.S. Pat. No. 4,935,346 titled "Minimum Procedure System for the Determination of Analytes" issued Jun. 19, 1990 to Roger Phillips et al. and U.S. Pat. No. 5,304,468 titled "Reagent Test Strip and Apparatus for Determination of Blood Glucose" issued Apr. 19, 1994 to Roger Phillips et al.

When a metal-coated support is to be employed as the substrate or webbing material (8), its thickness will typically range from about 0.002 to 0.014 in (51 to 356 $\mu$m), usually from about 0.004 to 0.007 in (102 to 178 $\mu$m), while the thickness of the metal layer will typically range from about 10 to 300 nm and usually from about 20 to 40 nm. A gold or palladium coating may be preferred for this purpose. For ease of manufacture, it may be preferred that the entire surface of substrate (8) is coated with metal.

Whatever the type substrate used, the subject systems and methods may be employed to dry a variety of different types of coating compositions applied to the surface of a substrate. In many embodiments, coating (10) comprises one or more reagent members of a signal producing system. A "signal producing system" is one in which one or more reagents work in combination to provide a detectable signal in the presence of an analyte that can be used to determine the presence and/or concentration of analyte. The signal producing system may be a signal producing system that produces a color that can be related to the presence or concentration of an analyte or it may be a signal producing system that produces an electrical current that can be related to the presence or concentration of an analyte. Other types of systems may be used as well.

A variety of different color signal producing systems are known. Representative color signal producing systems of interest include analyte oxidation signal producing systems. An "analyte oxidation signal producing system" is one that generates a detectable colorimetric signal from which the analyte concentration in the sample is derived, the analyte being oxidized by a suitable enzyme to produce an oxidized form of the analyte and a corresponding or proportional amount of hydrogen peroxide. The hydrogen peroxide is then employed, in turn, to generate the detectable product from one or more indicator compounds, where the amount of detectable product produced by the signal producing system, (i.e. the signal) is then related to the amount of analyte in the initial sample. As such, the analyte oxidation signal producing systems useable in the subject test strips may also be correctly characterized as hydrogen peroxide based signal producing systems.

As indicated above, the hydrogen peroxide based signal producing systems include an enzyme that oxidizes the analyte and produces a corresponding amount of hydrogen peroxide, where by corresponding amount is meant that the amount of hydrogen peroxide that is produced is proportional to the amount of analyte present in the sample. The specific nature of this first enzyme necessarily depends on the nature of the analyte being assayed but is generally an oxidase. As such, the first enzyme may be: glucose oxidase (where the analyte is glucose); cholesterol oxidase (where the analyte is cholesterol); alcohol oxidase (where the analyte is alcohol); lactate oxidase (where the analyte is lactate) and the like. Other oxidizing enzymes for use with these and other analytes of interest are known to those of skill in the art and may be employed. In those embodiments where the reagent test strip is designed for the detection of glucose concentration, the first enzyme is glucose oxidase. The glucose oxidase may be obtained from any convenient source (e.g., a naturally occurring source such as *Aspergillus niger* or Penicillum), or be recombinantly produced.

The second enzyme of the signal producing system is an enzyme that catalyzes the conversion of one or more indicator compounds into a detectable product in the presence of hydrogen peroxide, where the amount of detectable product that is produced by this reaction is proportional to the amount of hydrogen peroxide that is present. This second enzyme is generally a peroxidase, where suitable peroxidases include: horseradish peroxidase (HRP), soy peroxidase, recombinantly produced peroxidase and synthetic analogs having peroxidative activity and the like. See e.g., Y. Ci, F. Wang; Analytica Chimica Acta, 233 (1990), 299–302.

The indicator compound or compounds are ones that are either formed or decomposed by the hydrogen peroxide in the presence of the peroxidase to produce an indicator dye that absorbs light in a predetermined wavelength range. Preferably, the indicator dye absorbs strongly at a wavelength different from that at which the sample or the testing reagent absorbs strongly. The oxidized form of the indicator may be the colored, faintly-colored, or colorless final product that evidences a change in color. That is to say, the testing reagent can indicate the presence of analyte (e.g., glucose) in a sample by a colored area being bleached or, alternatively, by a colorless area developing color.

Indicator compounds that are useful in the present invention include both one- and two-component colorimetric substrates. One-component systems include aromatic amines, aromatic alcohols, azines, and benzidines, such as tetramethyl benzidine-HCl. Suitable two-component systems include those in which one component is MBTH, an MBTH derivative (see for example those disclosed in U.S. patent application Ser. No. 08/302,575, titled "incorporated herein by reference), or 4-aminoantipyrine and the other component is an aromatic amine, aromatic alcohol, conjugated amine, conjugated alcohol or aromatic or aliphatic aldehyde. Exemplary two-component systems are 3-methyl-2-benzothiazolinone hydrazone hydrochloride (MBTH) combined with 3-dimethylaminobenzoic acid (DMAB); MBTH combined with 3,5-dichloro-2-hydroxybenzenesulfonic acid (DCHBS); and 3-methyl-2-benzothiazolinone hydrazone N-sulfonyl benzenesulfonate monosodium (MBTHSB) combined with 8-anilino-1 naphthalene sulfonic acid ammonium (ANS). In certain embodiments, the dye couple MBTHSB-ANS is preferred.

Signal producing systems that produce a fluorescent detectable product (or detectable non-fluorescent substance, e.g. in a fluorescent background) may also be employed in the invention, such as those described in: Kiyoshi Zaitsu, Yosuke Ohkura, New fluorogenic substrates for Horseradish Peroxidase: rapid and sensitive assay for hydrogen peroxide and the Peroxidase. Analytical Biochemistry (1980) 109, 109–113.

Signal producing systems that produce an electric current (e.g., as are employed in electrochemical test strips) are of particular interest to the present invention. Such reagent systems include redox reagent systems, which reagent systems provide for the species that is measured by the electrode and therefore is used to derive the concentration of analyte in a physiological sample. The redox reagent system present in the reaction area typically includes at least enzyme(s) and a mediator. In many embodiments, the enzyme member(s) of the redox reagent system is an enzyme or plurality of enzymes that work in concert to oxidize the analyte of interest. In other words, the enzyme component of the redox reagent system is made up of a single analyte oxidizing enzyme or a collection of two or more enzymes that work in concert to oxidize the analyte of interest. Enzymes of interest include oxidases, dehydrogenases, lipases, kinases, diphorases, quinoproteins, and the like.

The specific enzyme present in the reaction area depends on the particular analyte for which the electrochemical test strip is designed to detect, where representative enzymes include: glucose oxidase, glucose dehydrogenase, cholesterol esterase, cholesterol oxidase, lipoprotein lipase, glycerol kinase, glycerol-3-phosphate oxidase, lactate oxidase, lactate dehydrogenase, pyruvate oxidase, alcohol oxidase, bilirubin oxidase, uricase, and the like. In many preferred embodiments where the analyte of interest is glucose, the enzyme component of the redox reagent system is a glucose oxidizing enzyme, e.g. a glucose oxidase or glucose dehydrogenase.

The second component of the redox reagent system is a mediator component, which is made up of one or more mediator agents. A variety of different mediator agents are known in the art and include: ferricyanide, phenazine ethosulphate, phenazine methosulfate, phenylenediamine, 1-methoxy-phenazine methosulfate, 2,6-dimethyl-1,4-benzoquinone, 2,5-dichloro-1,4-benzoquinone, ferrocene derivatives, osmium bipyridyl complexes, ruthenium complexes, and the like. In those embodiments where glucose in the analyte of interest and glucose oxidase or glucose dehydrogenase are the enzyme components, mediators of particular interest are ferricyanide, and the like.

Other reagents that may be present in the reaction area include buffering agents, citraconate, citrate, malic, maleic, phosphate, "Good" buffers and the like. Yet other agents that may be present include: divalent cations such as calcium chloride, and magnesium chloride; pyrroloquinoline quinone; types of surfactants such as Triton, Macol, Tetronic, Silwet, Zonyl, and Pluronic; stabilizing agents such as albumin, sucrose, trehalose, mannitol, and lactose.

For use in producing electrochemical test strips, a redox system including at least an enzyme and a mediator as described above is preferably used for coating (10). In solution, the system preferably comprises a mixture of about 6% protein, about 30% salts and about 64% water. The fluid most preferably has a viscosity of roughly 1.5 Cp. Still, it is to be understood that numerous kinds of solution may be dried with the inventive system. Most preferably, the solution comprises reagent-type solution. Indeed, the advantages of the present system are most apparent in connection with drying solution in which chemical activity must be maintained and with less viscous solutions, particularly solutions with a viscosity below 100 Cp.

Figure 3A:
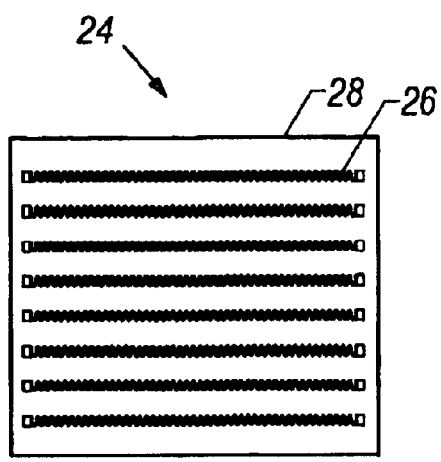
FIGS. 3A and 3B shows a bottom and side views, respectively, of a heating panel used in the IR dryer section.
Figure 3B:
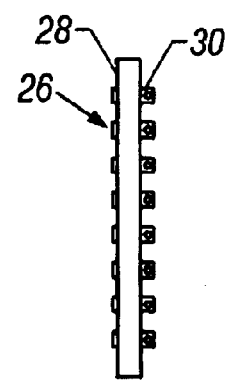

As for hardware to be used in the inventive system, FIGS. 3A and 3B show a preferred heating element used to deliver radiant energy within dryer section (6). The apparatus depicted is a panel or heater board (24) produced by Radiant Energy Systems (Wayne, N.Y.). For each board (24), 8 resistive heaters (26) are provided in connection with a ceramic thermowell (28) and associated electrical connections (30). The heaters are set to emit medium wavelength infrared energy. Instead of using one or more heater panels (24), a number of discrete heaters may be provided in succession. A suitable industrial-type infrared drying unit is also produced by Radiant Energy Systems as model number SFA-24. Alternately, one or more quartz tube heaters may be used to provide radiant (especially IR) energy for drying solution on webbing according to the present invention. A Sun-Mite™ heater model number FFH-912B by Fostoria (Comstock, Mich.) has proved effective in this regard.

Figure 4:
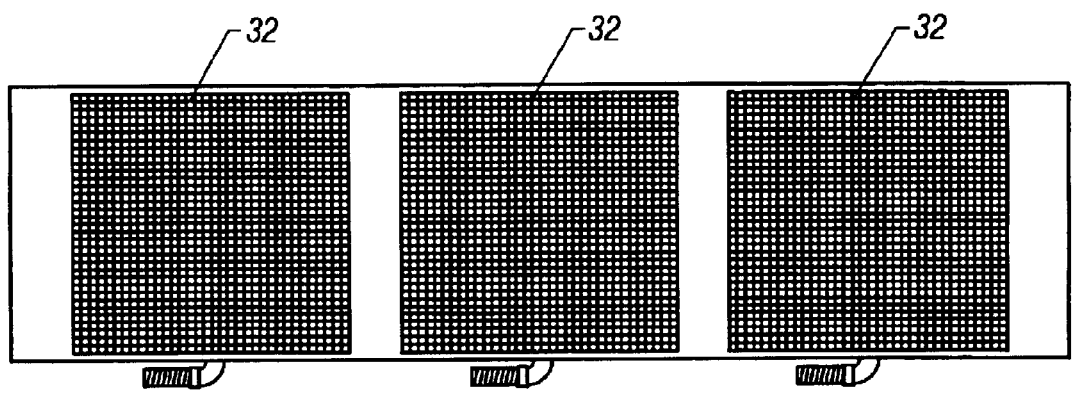
FIG. 4 shows a bottom view of a heating panel assembly used in the IR dryer section.

FIG. 4 shows a most preferred arrangement for heater elements. Three heater boards (24) are shown in series. Screens (32) are provided in front of the heater elements. When employing medium-wavelength infrared energy as preferred, the screens will have serve to rays, randomizing and making the energy application more even.

Figure 5:
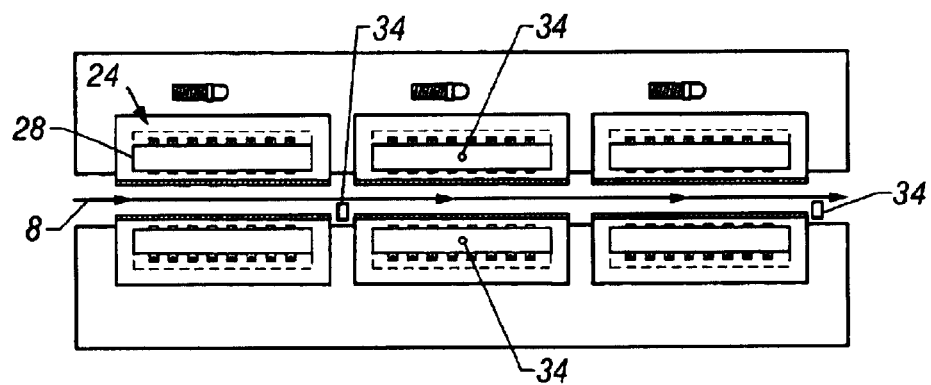
FIG. 5 shows a close-up of the IR dryer section from the backside.

FIG. 5 shows the apparatus in FIG. 4 in place within drying section (6). While six heater boards (24) are shown, energy is preferably only applied by elements above webbing (8) moving as indicated by the in-line arrows. Heater elements (26) are preferably positioned at a height between about 1 and 5 inches (25.4 and 127 mm) above the substrate upon which a coating has been deposited. More preferably, the spacing is between about 2 and 4 inches (50.8 and 101.6 mm). The amount of energy applied along webbing or substrate (8) is preferably between about 3.5 and 8 watts per square inch.

It is especially feasible to apply such high amounts of energy along the webbing when the webbing includes a surface that reflects much of the impinging. Using a reflective coating having a low emissivity such as platinum or palladium (about 0.1), high energy levels do not destroy the substrate. In some instances, it may be possible to use a substrate that transmits or is transparent to the energy and achieve the same effect.

In either event, solution (10) will typically easily absorb energy, i.e., have a high emissiviy (about 0.9). Accordingly, the IR energy applied has an effect where needed for drying, but not elsewhere.

Even under high-intensity drying conditions according to the present invention, it is possible to dry reagent coating without significantly affecting reagent activity. For instance, where protein-based reagents are included in the coating, the drying conditions employed are set so as not to denature the protein reagents beyond utility. More particularly, when the solution applied to the surface of the substrate includes an enzyme, activity of the enzymatic coating composition following drying by the present does not exhibit significant loss of activity as determined by DCIP/PMS methodology. The low absorptivity of the water in the coating and the effect of evaporative cooling on the solution upon water volatilization protect the proteins from denaturing.

While the latter effect would have some utility in drying with heated air alone, the other advantages applicable to drying with radiant energy are not present. Attempting rapid drying by air impingement techniques in effort to obtain the performance available with the present system would simply destroy the reagent coating activity or melt the webbing.

In the present invention, one or more temperature sensors (34) may be provided within dryer (6). Thermocouples and/or IR sensors may be employed. They may be used to monitor the ambient or air temperature within drying section or the temperature of the webbing. Even with reflective coating on the webbing having a high reflectance or low emissivity, the plastic upon which the coating is often applied (preferably polyester web) may be affected by temperatures above about 300° F. (150° C.). Feedback from the temperature sensors may be used to set or adjust dryer temperature to avoid damaging the webbing or reagent material coated thereon.

With the present invention, webbing processing speeds (i.e., the rate at which solution may be dried upon substrate) as high as 100 ft per minute may be achieved. More typically, processing speeds between 5 and 25–50 feet of substrate per minute are realized. The highest production speeds are available in connection with a setup in which the heater element(s) are used in connection one or more fans (36) that provide a non-disturbing airflow to break the vapor barrier of the solution being dried within radiant dryer section (6).

As noted above, one or more optional auxiliary dryer sections (22) may be used in the present invention. Typically, each comprises an air impingement dryer utilizing heated, forced air. Auxiliary dryers (22) are useful in speeding-up web processing by completing drying once the shape of the bead of solution laid-down on the substrate is substantially set by radiant-energy drying.

Normally, air impingement drying introduces a host of problems, especially in drying low viscosity solution. Simple air-impingement drying introduces both cross-web and down-web reagent stripe inconsistency as compared to the processes of the present invention.

At the most basic level, it is easily understood how high-velocity air impinging upon solution produces ripples, resulting in an uneven dried product along the length of a stripe of solution. The effect on the cross-section of dried reagent produced using air-impingement drying alone is, however, less obvious. Solution coating dried merely by air-impingement techniques exhibits an exaggerated U-shaped cross-section. Such a profile develops due to migration by osmosis of reagent over time toward edges that dry more rapidly.

As evidenced by improved consistency in reagent test strips made with reagent coating dried according to the present invention, a more uniform cross section results utilizing radiant energy. It is believed that the rapid drying potential offered by the present invention alleviates edge build-up by decreasing the available time for migration by osmosis to occur.

Also, down-web consistency is improved since solution is not disturbed when it is prone to movement. Even when auxiliary air-impingement dryers (22) are used in system (2), ripples or disturbances are not evident in dried reagent coating since the radiant section (6) applies sufficient energy to effectively set the shape of the coating.

Rapid shape setting with radiant energy also helps produce consistent product in another regard. When employing low viscosity or low surface tension solution with substrate that is hydrophilic or includes a hydrophilic coating (as may often be preferred in an electrochemical test strip, see U.S. patent application Ser. No. 09/497,269 titled, "Electrochemical Test Strip for Use in Analyte Determination" and U.S. Patent Application, titled "Solution Striping System"), the solution has a tendency to "wet-out" the substrate rapidly. Solution will tend to flow across and coat more area than desired, rather than maintaining a stripe or a bead upon application. The immediate drying effect achieved by the present invention by applying radiant energy at sufficient levels halts this, setting the boundaries of the reagent. Accordingly, costly reagent is not lost by migration. This approach offers significant improvement in dried stripe width accuracy and placement precision.

Furthermore, thicker coating regions of reagent may be achieved without requiring multiple coats of solution. In instances where it is not feasible to alter the surface tension of reagent or the surface energy of substrate to be coated, there are few alternatives to control stripe width and thickness. The ability to rapidly set the shape of thick coatings makes their application feasible.

In an electrochemical test strip, the dried reagent coating serves as an active layer in the electrochemical cell. Sufficient concentrations of the reagent components are required to achieve satisfactory results. It has been appreciated by the inventors hereof that low concentrations of reagent produce poor test results. The ability to apply relatively thicker reagent coating on substrate for inclusion in test strips thus offers potential for improved test strip accuracy.

Figure 6:
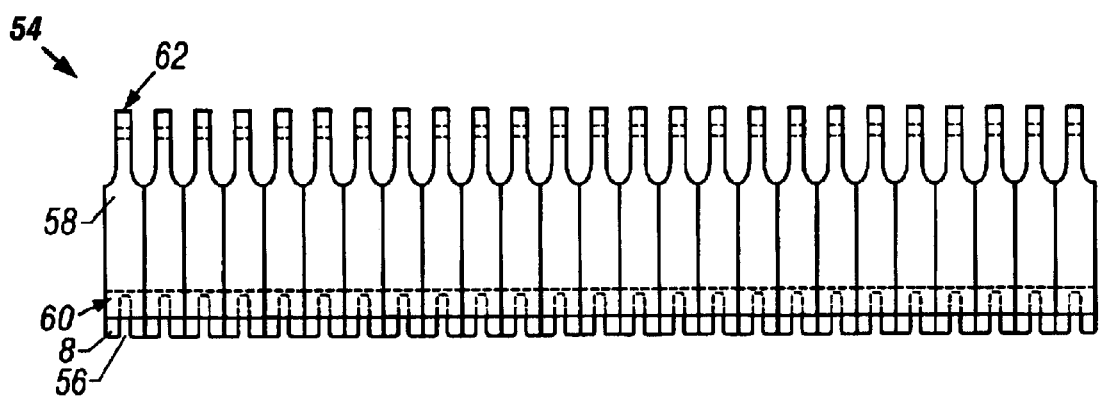
FIGS. 6 shows product of the inventive system in an intermediate stage of production.

Various forms of product may be produced in utilizing features of the invention. FIG. 6 shows a test strip precursor (54) in card for making electrochemical test strips. It comprises substrate or webbing material (8) as shown in FIG. 4 cut in two between the reagent stripes to form two 2⅛ in (5.4 cm) wide cards further modified with notches (56) as shown. The precursor may further comprise an opposing webbing (58) and a spacer (60) therebetween. Each are shown as cut, punched, or stamped to define test strip ends (62).

A continuous process (e.g., one in which various rolls of material are brought together to produce the precursor) such as in a continuous web process, or a discontinuous process (e.g., one in which the strip portions are first cut and then joined to each other) may be employed working with the precursor pieces. Other modes of multiple-component strip fabrication may also be employed.

The spacer preferably comprises a double-stick adhesive product. It may be fabricated from any convenient material, where representative materials include PET, PETG, polyimide, polycarbonate and the like. Webbing (8) is preferably plastic with sputtered-on palladium and functions as a "working" electrode, while webbing (58) is preferably gold coated plastic and functions as a "reference" electrode. Each webbing portion may have a thickness ranging from about 0.005 to 0.010 in (127 $\mu$m to 254 $\mu$m).

The test strip precursor may be in the form of a continuous tape or be in the form of a basic card (e.g., a parallelogram or analogous shape of shorter length) prior to the production stage shown in FIG. 6. As such, the length of the test strip precursor may vary considerably, depending on whether it is in the form of a tape or has a shorter shape (i.e., in the form of a card). The width of the test strip precursor may also vary depending on the nature of the particular test strip to be manufactured. In general, the width of the test strip precursor (or coated substrate alone) may range from about 0.5 to 4.5 in (13 to 114 mm). It may, of course, be wider, especially to accommodate additional stripes of solution.

As alluded to above, the width and depth of solution coating applied to substrate or webbing (8) may also vary depending on the nature of the product to be manufactured. For test strip production, the striping width will typically range from about 0.05 to 0.5 in (1.3 to 13 mm) and its thickness range from about 5 to 50 microns. Especially for use in electrochemical test strips, stripes or bands of aqueous reagent material are most preferably laid down in widths about 0.065 to 0.200 in (1.7 to 5.1 mm) wide and between about 15 and 25 microns deep when wet.

After being cut into a card, like that shown in FIG. 6, precursor (54) is singulated to produce individual test strips (62). Like the precursor, test strips may be cut manually or by automated means (e.g., with a laser singulation means, a rotary die cutting means, etc.). The precursor may be cut in stages as shown and described, or in a single operation. Patterns used for cutting may be set by a program, guide, map, image, or other direction means that directs or indicates how the test strip precursor should be cut into the reagent test strips. The pattern may or may not be visual on the test strip blank prior to cutting/singulation. Where the pattern is visible, the image may be apparent from a complete outline, a partial outline, designated points or markings of a strip. For further details as to how test strips may be manufactured, see U.S. patent application Ser. No. 09/737,179 titled "Method of Manufacturing Reagent Test Strips."

Figure 7:
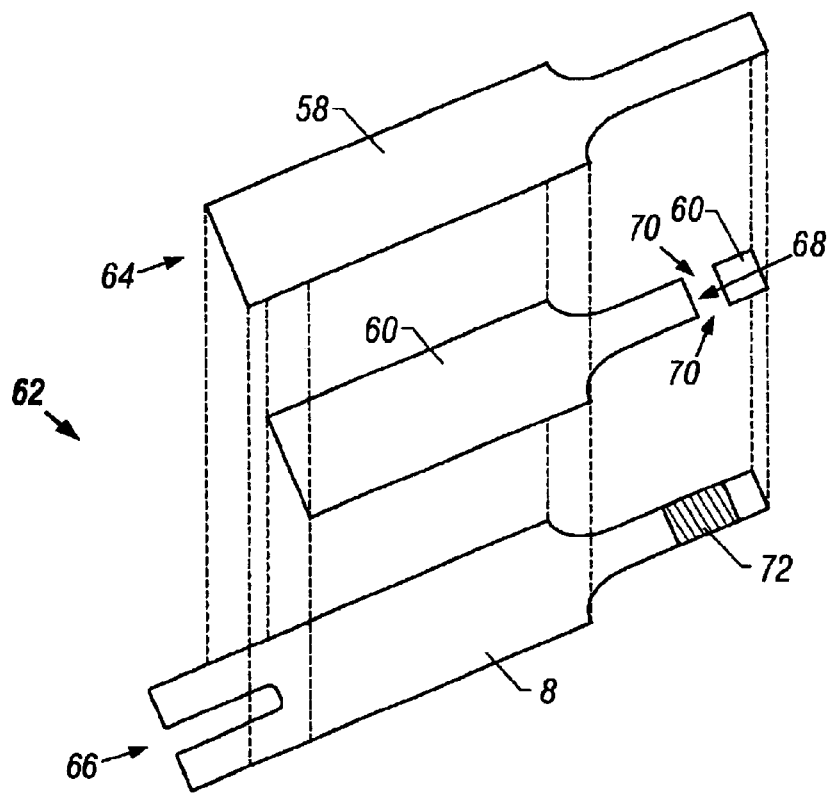
FIG. 7 shows an exploded perspective view of a test strip made using the present invention.

FIG. 7 shows an exploded view of a single representative electrochemical test (62). The subject test trip comprising a reference electrode (64) and working electrode (66) separated by spacer member (60) which is cut away to define a reaction zone or area (68) in communication with side ports (70) defined by a break in the spacer's coverage adjacent reagent patch (72) formed from a dried solution stripe.

To use such an electrochemical test strip, an aqueous liquid sample (e.g., blood) is placed into the reaction zone. The amount of physiological sample that is introduced into the reaction area of the test strip may vary, but generally ranges from about 0.1 to 10 $\mu$l usually from about 0.3 to 0.6 $\mu$l. The sample may be introduced into the reaction area using any convenient protocol, where the sample may be injected into the reaction area, allowed to wick into the reaction area, or be otherwise introduced through the ports.

The component to be analyzed is allowed to react with the redox reagent coating to form an oxidizable (or reducible) substance in an amount corresponding to the concentration of the component to be analysed (i.e., analyte). The quantity of the oxidizable (or reducible) substance present is then estimated by an electrochemical measurement.

The measurement that is made may vary depending on the particular nature of the assay and the device with which the electrochemical test strip is employed (e.g., depending on whether the assay is coulometric, amperometric or potentiometric). Measurement with the strip (62) is preferably accomplished by way of a meter probe element inserted between the electrode members to contact their respective interior surfaces. Usually, measurement is taken over a given period of time following sample introduction into the reaction area. Methods for making electrochemical measurements are further described in U.S. Pat. Nos.: 4,224,125; 4,545,382; and 5,266,179; as well as WO 97/18465 and WO 99/49307 publications.

Following detection of the electrochemical signal generated in the reaction zone, the amount of the analyte present in the sample is typically determined by relating the electrochemical signal generated from a series of previously obtained control or standard values. In many embodiments, the electrochemical signal measurement steps and analyte concentration derivation steps, are performed automatically by a device designed to work with the test strip to produce a value of analyte concentration in a sample applied to the test strip. A representative reading device for automatically practicing these steps, such that user need only apply sample to the reaction zone and then read the final analyte concentration result from the device, is further described in copending U.S. application Ser. No. 09/333,793 filed Jun. 15, 1999.

The reaction zone in which activity occurs preferably has a volume of at least about 0.1 μl, usually at least about 0.3 μl and more usually at least about 0.6 μl, where the volume may be as large as 10 μl or larger. The size of the zone is largely determined by the characteristics of spacer (60). While the spacer layer is shown to define a rectangular reaction area in which the aforementioned activity occurs, other configurations are possible, (e.g., square, triangular, circular, irregular-shaped reaction areas, etc.). The thickness of the spacer layer generally ranges from about 0.001 to 0.020 in (25 to 500 μm), usually from about 0.003 to 0.005 in (76 to 127 μm). The manner in which the spacer is cut also determines the characteristics of ports (70). The cross-sectional area of the inlet and outlet ports may vary as long as it is sufficiently large to provide an effective entrance or exit of fluid from the reaction area.

As depicted, the working and reference electrodes are generally configured in the form of elongate strips. Typically, the length of the electrodes ranges from about 0.75 to 2 in (1.9 to 5.1 cm), usually from about 0.79 to 1.1 in (2.0 to 2.8 cm). The width of the electrodes ranges from about 0.15 to 0.30 in (0.38 to 0.76 cm), usually from about 0.20 to 0.27 in (0.51 to 0.67 cm). In certain embodiments, the length of one of the electrodes is shorter than the other, wherein in certain embodiments it is about 0.135 in (3.5 mm) shorter. Preferably, electrode and spacer width is matched where the elements overlap. In a most preferred embodiment, electrode (64) is 1.365 in (35 cm) long, electrode (66) is 1.5 in (3.8 cm) long, and each are 0.25 in (6.4 mm) wide at their maximum and 0.103 in (2.6 mm) wide at their minimum, reaction zone (68) and ports (70) are 0.065 in (1.65 mm) wide and the reaction zone has an area of about 0.0064 in$^2$ (0.041 cm$^2$). The electrodes typically have a thickness ranging from about 10 to 100 nm, preferably between about 18 to 22 nm. The spacer incorporated in the strip is set back 0.3 in (7.6 mm) from the end electrode (66), leaving an opening between the electrodes that is 0.165 in (4.2 mm) deep.

Test strips according to the present invention may be provided in packaged combination with means for obtaining a physiological sample and/or a meter or reading instrument such as noted above. Where the physiological sample to be tested by a strip is blood, the subject kits may include a tool such as a lance for sticking a finger, a lance actuation means, and the like. Further, test strip kits may include a control solution or standard (e.g., a glucose control solution that contains a standardized concentration of glucose). Finally, a kit may include instructions for using test strips according to the invention in the determination of an analyte concentration in a physiological sample. These instruction may be present on one or more of container(s), packaging, a label insert or the associated with the subject test strips.

Though the invention has been described in reference to a single example, optionally incorporating various features, the invention is not to be limited to the set-up described. The invention is not limited to the uses noted or by way of the exemplary description provide herein. It is to be understood that the breadth of the present invention is to limited only by the literal or equitable scope of the following claims.

That being said, we claim:

1. A method of producing a reagent coated substrate comprising:

coating a substrate with reagent in solution, and exposing said solution to radiant energy provided by at least one radiant energy heater, wherein airflow sufficient only to break a vapor barrier of the solution is directed at said solution while exposed to said radiant energy.

2. A method of producing a reagent coated substrate comprising:

coating a substrate with reagent in solution, and exposing said solution to radiant energy provided by at least one radiant energy heater, wherein said substrate is provided in a roll, and the method further comprises feeding said roll past said radiant energy source.

3. A method of producing a reagent coated substrate comprising:

coating a substrate with reagent in solution, and exposing said solution to radiant energy provided by at least one radiant energy heater, wherein said substrate is provided in a roll, and the method further comprises feeding said roll past said radiant energy source, wherein said feeding of said substrate is performed at a rate between about 5 and 50 feet per minute.

4. The method of claim 1, 2 or 3, wherein said reagent is provided in at least one stripe.

5. The method of claim 1, 2 or 3, wherein said substrate includes a reflective surface.

6. The method of claim 5, wherein said radiant energy is infrared energy delivered at an intensity of at least 3.5 W/in$^2$.

* * * * *